United States Patent [19]

Yagami et al.

[11] Patent Number: 5,738,100
[45] Date of Patent: Apr. 14, 1998

[54] ULTRASONIC IMAGING CATHETER

[75] Inventors: Hiroyuki Yagami; Hiroshi Katsumata, both of Nakai-machi; Hideshi Obitsu, Fujinomiya, all of Japan

[73] Assignee: Terumo Kabushiki Kaisha, Tokyo, Japan

[21] Appl. No.: 672,119

[22] Filed: Jun. 27, 1996

[30] Foreign Application Priority Data

Jun. 30, 1995 [JP] Japan ................................. 7-165598
Jun. 30, 1995 [JP] Japan ................................. 7-165619

[51] Int. Cl.⁶ .............................................. A61B 8/12
[52] U.S. Cl. .................................................. 128/662.06
[58] Field of Search ................. 128/660.03, 662.06, 128/660.1, 662.03

[56] References Cited

U.S. PATENT DOCUMENTS

| | | |
|---|---|---|
| 4,899,757 | 2/1990 | Pope, Jr. et al. . |
| 4,951,677 | 8/1990 | Crowley et al. . |
| 5,049,130 | 9/1991 | Powell . |
| 5,095,911 | 3/1992 | Pomeranz . |
| 5,168,878 | 12/1992 | Takano . |
| 5,176,140 | 1/1993 | Kami et al. . |
| 5,255,681 | 10/1993 | Ishimura et al. . |
| 5,290,230 | 3/1994 | Ainsworth et al. . |
| 5,368,035 | 11/1994 | Hamm et al. ............... 128/662.06 |
| 5,368,037 | 11/1994 | Eberle et al. ............... 128/662.06 |
| 5,372,138 | 12/1994 | Crowley et al. ............ 128/662.06 |
| 5,437,282 | 8/1995 | Koger et al. . |
| 5,451,209 | 9/1995 | Ainsworth et al. . |
| 5,455,155 | 10/1995 | Sieben ....................... 128/662.06 |
| 5,458,585 | 10/1995 | Salmon et al. ............. 128/662.06 |
| 5,546,947 | 8/1996 | Yagami et al. ............. 128/662.06 |
| 5,558,093 | 9/1996 | Pomeranz ................. 128/662.06 X |
| 5,570,693 | 11/1996 | Jang et al. ................. 128/662.06 X |

FOREIGN PATENT DOCUMENTS

| | | | |
|---|---|---|---|
| 0 608 853 | 8/1994 | European Pat. Off. . | |
| 0 646 349 | 4/1995 | European Pat. Off. . | |
| 4307045 | 10/1992 | Japan ........................... | 128/662.06 |
| 5-92003 | 4/1993 | Japan . | |
| 5-212036 | 8/1993 | Japan . | |
| 6090953 | 4/1994 | Japan ........................... | 128/662.06 |
| 89/04143 | 5/1989 | WIPO . | |
| 91/00051 | 1/1991 | WIPO . | |
| 93/16642 | 9/1993 | WIPO . | |

*Primary Examiner*—Francis Jaworski
*Attorney, Agent, or Firm*—Burns, Doane, Swecker & Mathis, LLP

[57] ABSTRACT

An ultrasonic imaging catheter includes an outer sheath that is adapted to be inserted into a body cavity, and a drive shaft that is positioned in the outer sheath for transmitting mechanical driving force. The catheter is also provided with first and second elastic members. The first elastic member is disposed at the tip portion of the outer sheath while the second elastic member that is secured to the housing containing a transducer has a free end that is inserted into the first elastic member. The portion of the catheter between the housing and the first elastic member at the free end of the catheter is thus reinforced to improve flexibility and kinking of the catheter. The housing can be made of insulating ceramic material so that the insulation and resistance of the housing is high. Thus, a short between the electrodes of the oscillator does not occur even when the oscillator is in direct contact with the housing.

26 Claims, 12 Drawing Sheets

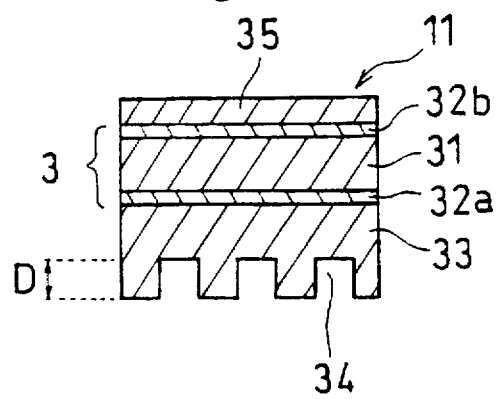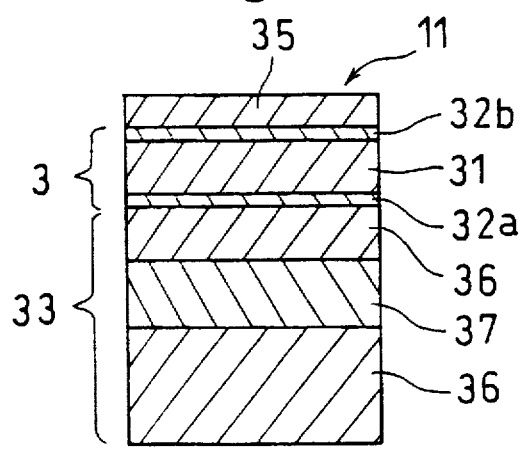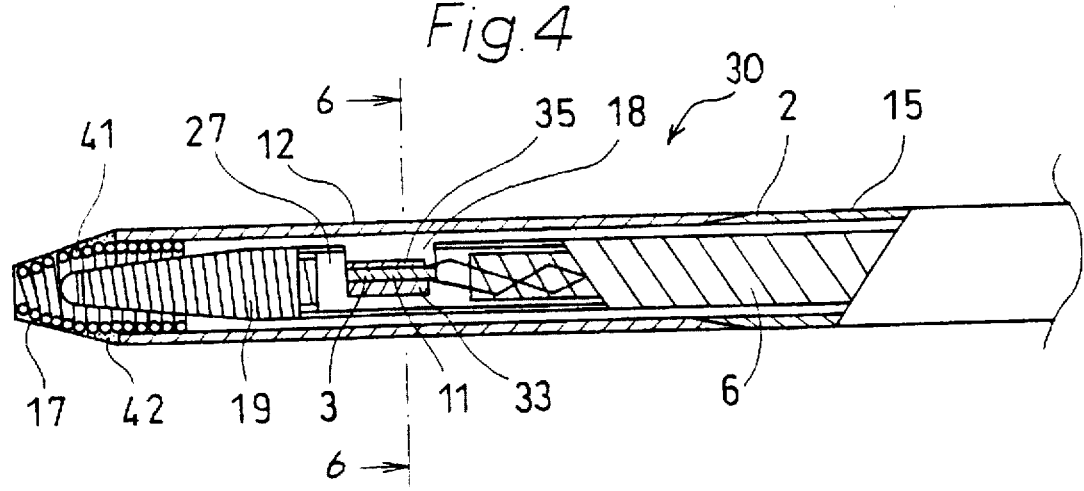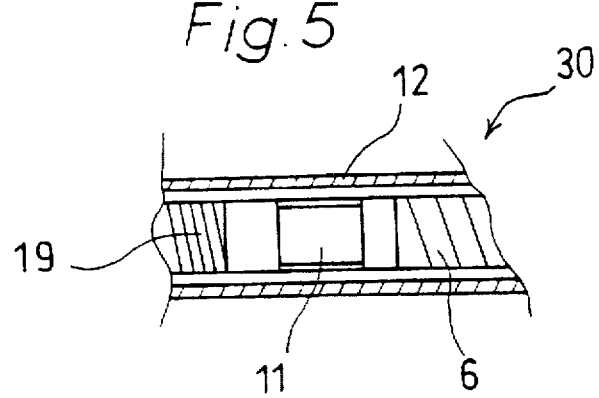

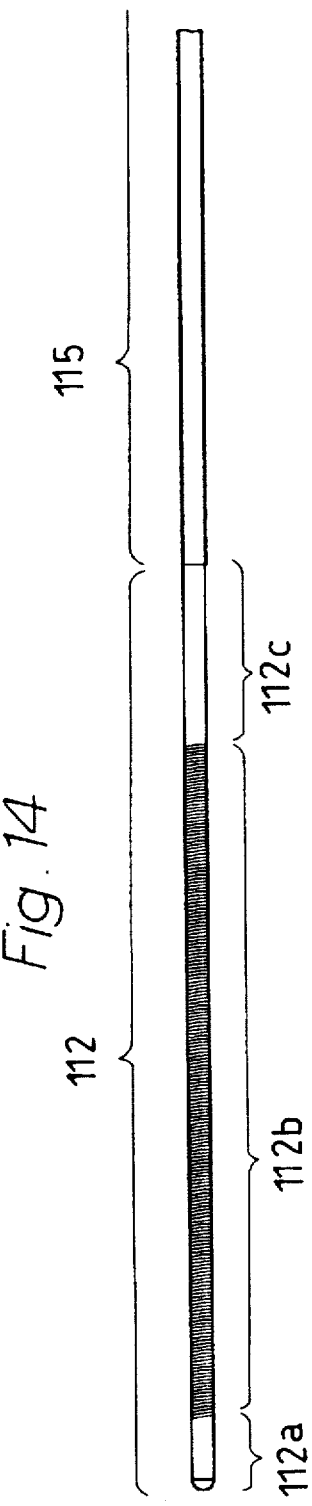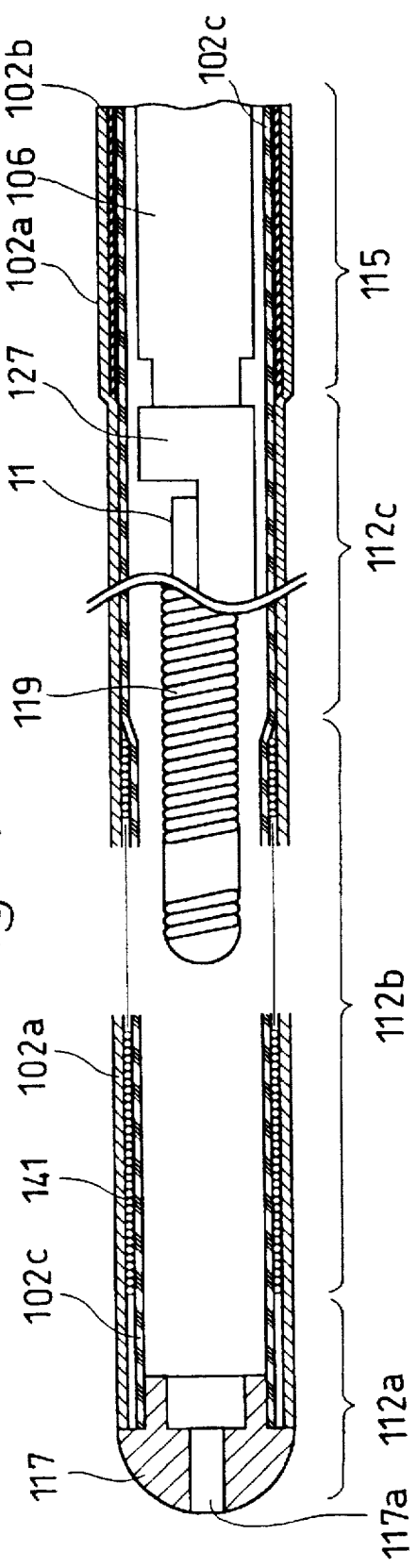

ULTRASONIC IMAGING CATHETER

BACKGROUND OF THE INVENTION

The present invention relates to an ultrasonic imaging catheter inserted into a body cavity such as a vessel or a vas.

It has known that the ultrasonic imaging catheter is inserted into a thin vessel such as a coronary artery of a heart or the vas such as a bile duct to form a tomogram of the vessel or the vas or to make a measurement of a blood flow therein. The ultrasonic imaging catheter comprises, for example as shown in FIGS. 20 and 21, a hollow outer sheath 2, an ultrasonic wave oscillator 3 disposed inside of a tip of the outer sheath 2, a drive shaft 6 of transferring driving force for rotating directly the oscillator 3 or an ultrasonic wave reflector 4, and signal cables 7 interconnecting the oscillator 3 and an outer electrical circuit 5. An outer driver 8 mechanically drives the drive shaft to scan an ultrasonic wave emitted from the oscillator.

It is desirable to make a tip portion of the catheter to be inserted into the blood vessel flexible to improve movement of the catheter within the blood vessel. It is further desirable that the tip portion of the catheter can be found under an X-ray fluoroscopy. Some catheters, thereby, have a mark for adding a contrast on a catheter body to point the position of the catheters. Some catheter have a metal plate, ring-shaped or coil-shaped at the tip portion of the catheter that can point the X-ray contrast. An ultrasonic imaging catheter, as shown in FIGS. 20 and 21, has an elastic metallic member of coil-shaped or a metallic piece 14 for adding the contrast at the tip portion thereof The ultrasonic wave is transmitted and received through a portion 12 of an outer sheath 2 of the ultrasonic imaging catheter. The portion 12 made of material having a good permeability for the ultrasonic wave such as olefin system resin and fluoride system resin. The thickness of the portion 12 is 100 μm or less because the thinner the portion 12, the better in permeability for the ultrasonic wave. The mechanical strength of the portion 12, therefore, is lower than a handle side shale 15 of the catheter and is liable to kink. Furthermore, the ultrasonic imaging catheter has a stiff portion such as the ultrasonic wave oscillator. Therefore, a mechanical property of the catheter fails to change gradually among the stiff portion of the oscillator 3 or the like and the tip portion of the outer sheath 2 in which a coil-like elastic member is disposed. The ultrasonic imaging catheter hence fails to perform a preferable bend and is liable to kink so that the ultrasonic imaging catheter is poor in handling.

U.S. Pat. No. 5,095,011 discloses an ultrasonic imaging catheter that comprises an outer sheath, a housing secured to the outer sheath, an elastic member connected to a tip portion of the housing. The housing of the catheter is stiff and long such that a tip portion of the catheter including the housing is poor in flexibility and is hard to bend.

The catheter without any stiff housings as shown in FIG. 20 is preferable from a view point of the flexibility.

It is a first object of the present invention to provide an ultrasonic imaging catheter of preferable handling because of improved flexibility and bend between a stiff portion of a tip side including the oscillator and an elastic member at a tip of the catheter.

A conventional ultrasonic imaging catheter comprises ultrasonic oscillators inside of a housing. Most of the housings of the conventional type are cylindrical to improve sliding between the housing and an outer sheath (See JP-A 5-212036 and JP-A 5-92003). A drive shaft 6 is formed with a metallic coil made of stainless steel (SUS304, SUS316, etc.) or the like. The housing and the drive shaft are connected to each other by brazing or welding so that the housing is made of stainless steel (SUS304, SUS316, etc.) or the like similar to the drive shaft. One of electrodes of the oscillator secured to the housing must not be contacted with the housing to prevent a short among electrodes of the oscillator. To realize this, a method of packing the oscillator with a case of insulating material that is secured to the housing is carried out. According to the method, the oscillator is limited in an outer diameter to be small because of the thickness of the insulating material. A depth of transparency of the ultrasonic wave in an object to be measured and divergence of the ultrasonic wave in an azimuth direction are very important in the ultrasonic imaging catheter. In particular, it is desirable to use an oscillator largest in size to minimize the divergence in the azimuth direction and to deepen in the depth of the transparency of the ultrasonic wave when the ultrasonic catheter is thin in diameter, particularly 1 mm or less in outer diameter.

It is a second object of the present invention to provide an ultrasonic imaging catheter of particularly thin diameter in which the oscillator is permitted to be larger in size than a conventional one to deepen the transparency in the object and to minimize the divergence in the azimuth direction of the ultrasonic wave.

SUMMARY OF THE INVENTION

The first object of the present invention is achieved by the following.

An ultrasonic imaging catheter comprises an outer sheath to be inserted into a body cavity, a drive shaft inserted into the outer sheath for transmitting mechanical driving force from a proximal side to a tip side thereof the drive shaft being rotatable by an outer driving source; a housing secured to the drive shaft in which an ultrasonic wave oscillator or both the ultrasonic wave oscillator and an ultrasonic wave reflector are disposed, the housing being located inside of a tip side of the outer sheath, a first elastic member disposed at a tip of the outer sheath, and a second elastic member disposed at a tip portion of the housing, the second elastic member extending toward a tip side of the catheter, A tip of the second elastic member is located inside of the first elastic member.

The first object of the present invention is achieved by the following.

An ultrasonic imaging catheter comprises an outer sheath assembly having an outer layer and an tuner layer, a drive shaft inserted into the outer sheath assembly, a housing cured to the drive shaft in which an ultrasonic wave oscillator are disposed, the housing being located inside of a tip side of the outer sheath assembly, a first elastic member located at a tip portion of the outer sheath assembly and inserted between the outer layer and the inner layer, and a second elastic member disposed at a tip portion of the housing, the second elastic member extending toward a tip side of the catheter, a tip of the second elastic member is located inside of the first elastic member.

The second object of the present invention is achieved by the following.

An ultrasonic imaging catheter comprises an outer sheath to be inserted into a body cavity, a drive shaft inserted into the outer sheath for transmitting mechanical driving force from a proximal side to a tip side thereof the drive shaft being rotatable or movable in an axial direction thereof by an outer driving source, and a housing secured to the drive shaft in which an ultrasonic wave oscillator or both the

3 ultrasonic wave oscillator and an ultrasonic wave reflector are disposed, the housing being located inside of a tip side of the outer sheath, the housing comprising insulating material

BRIEF DESCRIPTION OF THE DRAWINGS

The present invention is illustrated in the accompanying drawings, in which:

FIG. 3A is a sectional view of showing a structure of a transducer used in the ultrasonic imaging catheter of the present invention.

FIG. 3B is a sectional view of showing a structure of another transducer used in the ultrasonic imaging catheter of the present invention.

FIG. 4 is a sectional view of a tip portion of an ultrasonic imaging catheter of another embodiment of the present invention.

FIG. 5 is a plane view showing a transducer of the ultrasonic imaging catheter shown in FIG. 4 and vicinities of the transducer.

FIG. 14 is an enlarged view showing a tip portion of the ultrasonic imaging catheter shown in FIG. 13 and vicinities of the tip portion FIG. 15 is an enlarged and sectional view of the tip portion of the catheter shown in FIG. 13.

DESCRIPTION OF THE PREFERRED EMBODIMENTS

An ultrasonic imaging catheter of the present invention is described hereinbelow with regard to the attached drawings.

The ultrasonic imaging catheter 1 of this invention comprises an outer sheath 2 to be inserted into a body cavity, a drive shaft or driving shaft 6 inserted into the outer sheath 2, a housing 27 secured at a tip of the drive shaft 6, a handle portion (a connector) 20 connected with a proximal end of the outer sheath 2.

Figure 1:
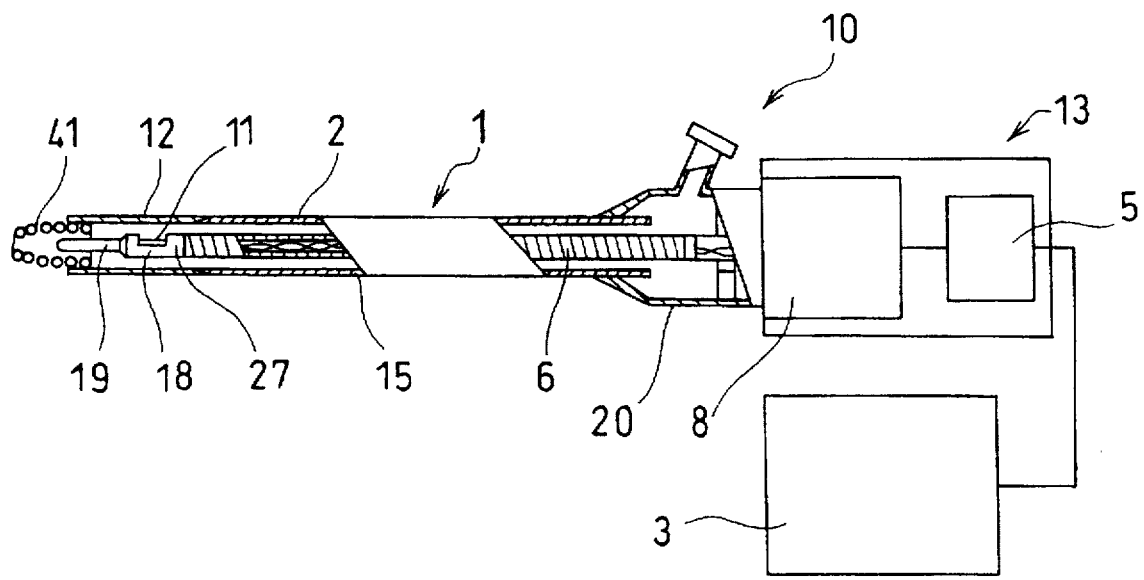
FIG. 1 is a partially sectional view of an ultrasonic imaging catheter of the present invention attached to an outer unit.

FIG. 1 shows an ultrasonic imaging catheter system 10 configured by attaching the ultrasonic imaging catheter 1 to an outer unit 13.

A housing 27 is disposed inside of a tip portion of the outer sheath 2 of the catheter. A transducer 11 is disposed in the housing 27. The transducer 11 has a function as an ultrasonic wave oscillator for transmitting and receiving an ultrasonic wave. The housing 27 is connected at a free end of the coil shaped drive shaft 6.

The drive shaft 6 is formed with two layers of plates spiraled twice and the plates are made of stainless steel (SUS304, SUS316, etc.) or the like. The drive shaft preferably has breaking strength of 0.4 kgf or more. The drive shaft 6 may be formed with a wire or plate, which is made of metal or resin, spiraled once or multiply in a coil manner or in a blade manner. The drive shaft may be formed by winding a signal cable mentioned below around the wire having the breaking strength of 0.4 kgf or more.

The signal cable 7 formed by stranding two leads 7a and 7b is threaded into drive shaft 6. An end of the signal cable 7 positioned on the tip side of the catheter is connected with an oscillator formed in the transducer 11. Another end of the signal cable 7 positioned on the proximal side (on the handle side) of the catheter is connected with terminals 21 and 22 of the operational member 20. In more detail, as show in FIG. 2, a tubular member formed by insulation material is inserted and fixed into the proximal end of the shaft 6. The terminal 22 is fixed to the proximal edge of the tubular member. The terminal 21 is fixed on the side surface of the middle portion of the tubular member. The end of the lead 7a is connected by the terminal 22. The end of the lead 7b is connected to the terminal 21 through an opening formed on the side of the tubular member.

Figure 2:
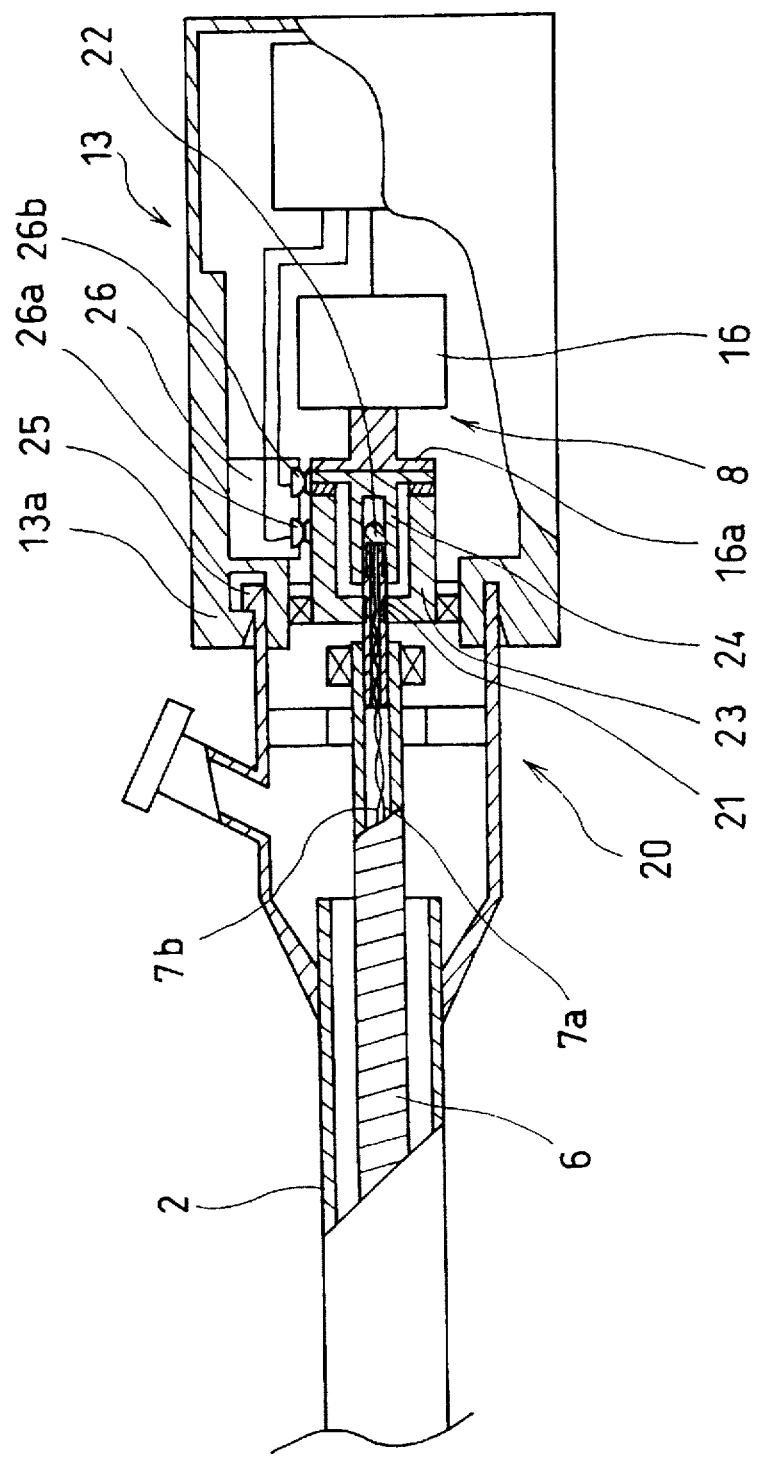
FIG. 2 is a partially sectional view of a handle portion (a connector) and the outer unit of the ultrasonic imaging catheter of the present invention.

The handle portion (the connector) 20 has, as shown in FIG. 2, a projection 25 to be engaged with an arresting member 13a of the outer unit 13. The projection 25 and the arresting member 13a are connected in a detachable manner.

The outer unit 13 comprises a transmitting-receiving circuit 5 and a driving source 8 including a motor 16. The outer unit 13 is electrically connected with a console 3 having a signal processing circuit and an image displaying unit.

The motor 16 as an outer driving source has a rotor (a rotating plate) 16a. A first cylindrical terminal 24 is secured at the center of the rotating plate 16a and a second cylindrical terminal 23 is secured on the rotating plate 16a around the first cylindrical terminal 24 without any contact therebetween. The cylindrical terminals 23 and 24 rotate together with the rotating plate.

A rotational slip terminal member 26 that comprises a slip ring or the like connected with the transmitting-receiving circuit 5 is disposed inside of the outer unit 13. The terminal member 26 has a first terminal 26a and a second terminal 26b. The first terminal 26a is in contact with the second cylindrical terminal 23 on the rotational plate. The second terminal 26b is in contact with the first cylindrical terminal 24 on the rotational plate. The contacts between the respective terminals are kept while the rotational plate rotates.

The tubular member having the terminals 21 and 22 secured to the drive shaft 6 is engaged with an opening of the first cylindrical terminal 24 on the rotational plate. The proximal portion (terminal 21) of the tubular member is allowed to enter into the second terminal 23 on the rotational plate and the proximal portion is engaged with a circular rib formed near the free end of an opening of the cylindrical terminal 23. The drive shaft 6, thereby, is connected with the rotational plate of the motor 16 in a detachable manner. Rotational force of the motor is transmitted to the drive shaft through the rotational plate and two cylindrical terminals 23 and 24.

The housing 27 is pipe-shaped and has an outer diameter approximately equal to that of the drive shaft 6. A fixing portion 18 of the transducer 11 is formed by cutting the pipe-shaped member in an axial direction around the center by a predetermined length and in a radial direction by almost a half of a circle of the pipe-shaped member. The housing 27 is made of metal, resin or ceramics or the like. The housing 27 is made of metallic material such as stainless steel (SUS304, SUS316, etc.) or ceramic material such as alumina and zirconia m a view point of connection strength and reinforcing the transducer 11.

A first elastic member 41 of coil-shaped and spiraled once is formed at the free end of the catheter 2 (at the tip of the outer sheath). The first elastic member 41 protrudes to the tip of the outer sheath 2. A second elastic member 19 is connected with the tee end of the housing 27. The second elastic member 19 extends toward a tip direction of the catheter. The second elastic member extends up to inside of the first elastic member to reinforce the first elastic member 41. That is, a tip of the second elastic member 19 is positioned within the first elastic member 41.

The second elastic member 19 is a rod-like member and is made of metal having an elastic property such as stainless steel (SUS304, SUS316, etc.), super elastic metal such as Ni—Ti system alloy, resin such as polyacetal or the like. The elastic member 19 is preferably made of the super elastic metal such as Ni—Ti system alloy m view points of connection strength with the housing 27 and its own elasticity. The second elastic member 19 is connected at the tip portion of the housing 27 by adhering, brazing, welding or the like. It is preferable to insert the elastic member 19 by about 0.5 to 20 mm long into the coil-like elastic member 41 that is connected to an inner surface of the outer sheath 2 of the catheter.

The first elastic member 41 is secured to the outer sheath 2 as inserting a proximal end of the member 41 into the open end of the sheath 2. A distal end of the first elastic member 41 protrudes to the open end of the sheath 2. It is preferable to shorten a length of the connecting portion between the coil-like elastic member 41 and the open end of the outer sheath 2 while keeping enough connection strength therebetween. It is preferable to be about 0.5 to 10 mm long. The coil-like elastic member 41 is conical shape and its diameter tapers in the tip direction.

The coil-like elastic member 41 at the tip of the catheter is made of the material similiar to that of the elastic member 19. Metal such as Pt, Ir, Au or alloy thereof (high X-ray contrast material) is preferable to the material of the elastic member 41 in a point of giving the contrast in an image formed by an X-ray.

In the ultrasonic imaging catheter 1 of the present invention, the tip of the rod-like elastic member 19 always positioned within the coil-like elastic member 41 even when the catheter bends. A portion between the housing 27 and the coil-like elastic member 41 at the tip of the catheter is improved in bending and kinking in comparison with the conventional catheter that comprises only an outer sheath and no elastic members.

In particular, the second elastic member 19 located from the tip of the housing 27 to inside of the first elastic member 41 is disposed in the device of the present embodiment. A section from the end of the housing 27 to the tip of the catheter is improved in bending because no portion in which physical property varies radically is formed.

The outer sheath 2 of the catheter comprises an ultrasonic wave transmitting-receiving portion 12 of the tip side and a main body 15 of the handle side. The portion 12 and the body 15 re allowed to be formed with different material, The outer sheath 2 or the main body 15 of the sheath is formed with so-called catheter material. That is, a tube made of polyolefin resin, polyurethane resin, polyacetal resin, polyimide resin, fluoride resin, or the like, a tube made of stainless steel (SUS304, SUS316, etc.) or the like, a tube made of super elastic metal such as Ni—Ti system alloy, and a combined tube configured by winding a resin wire or a stainless steel (SUS304, SUS316, etc.) wire or the like in a coil manner or in a blade manner. The thickness of the sheath 2 and 15 is 30 to 300 μm and it is desirable that the sheath has at least 0.4 kgf of tensile break strength. It is desirable to form the ultrasonic wave transmitting-receiving portion 12 at the tip side of the catheter with the material of good permeability in the ultrasonic wave, i.e. polyolefin system resin, polyurethane system resin or fluoride system resin. The thickness of the resin to form the transmitting-receiving portion 12 is about 10 to 100 μm in preferable.

It is possible to coat an outer surface and an inner surface of the outer sheath 2 (in particular the outer surface) with hydrophile resin, fluoride resin or silicone resin or the like in 1 to several tens μm thickness. The sliding resistance of the outer and inner surfaces of the outer sheath 2 decreases by the treatment mentioned above. It is allowed to coat or fix the outer surface of the outer sheath with antithrombus material. Coating with the antithrombus material is realized by coating the outer surface of the shaft with a resin including the antithrombus such as heparin.

FIG. 3A is a sectional view showing a configuration of a transducer 11 utilized for the ultrasonic imaging catheter 1 of the present invention, The transducer 11 includes an ultrasonic wave oscillator 3. The oscillator performs transmitting and receiving of the ultrasonic wave. The oscillator 3 is formed by evaporating or printing electrodes 32 on both surfaces of a piezoelectric layer 31 of a rectangular PZT. The piezoelectric layer 31 may be circularly shaped. A back layer 33 is disposed backside of the oscillator 3 to absorb or to attenuate the ultrasonic wave. The back layer 33 is made of epoxy system resin, urethane system resin, acrylic system resin, or the like or resin in which metallic powder or inorganic powder is mixed. The back layer 33 in FIG. 3A forms projections and recesses to offset a reflected wave from a back side of the back layer 33 by interference. A difference D in thickness between the projections and recesses is λ/4 where λ is a wave length of the ultrasonic wave at a transmitting frequency in the back layer 33. The back layer 33 may be formed, as shown in FIG. 3B, by alternating a low acoustic impedance layer 36 ($Z=8 \times 10^6$ Kg/m²s or less) and a high acoustic impedance layer 37 ($Z=20 \times 10^6$ kg/m²s or more) to attenuate influence of the reflected wave form the back side of the back layer 33.

An acoustic alignment layer 35 so-called is disposed on an acoustic emission surface of the oscillator 3. The acoustic alignment layer 35 is so constructed that its thickness (D) equals to $\lambda/4$ where $\lambda$ is a wave length of the ultrasonic wave at the transmitting frequency in the alignment layer. Only one acoustic alignment layer is shown in FIGS. but it is allowed to form it with two or more layers.

Next, explanation for an ultrasonic imaging catheter 30 of another embodiment of the present invention will be made by referring to FIGS. 4, 5 and 6. It is noted that basic configuration of the ultrasonic imaging catheter 30 is similar to the ultrasonic imaging catheter 1 shown in FIGS. 1 and 2 mentioned above.

In the ultrasonic imaging catheter 30 of the embodiment, a transducer 11 is secured to a housing 27 with an adhesive or the like in a manner that deviation in a perpendicular direction of an ultrasonic wave transmitting-receiving surface of the transducer with respect to an axial direction of the ultrasonic imaging catheter 11 should be kept about ±10°. The housing 27 is connected with a tip of a drive shaft 6 with at least 0.4 kgf of connection strength by adhering, brazing or welding.

In the ultrasonic imaging catheter 30 of the embodiment, a coil-like elastic member 19 is connected with a free end of the housing 27. The elastic member 19 tapers in diameter towards the tip of the catheter. The coil-like elastic member 19 is formed with monolayer or multilayer elastic strip and spiraled once or multiply. It is preferable to spiral the outer most layer in the direction by which the strip is loosened as the drive shaft rotates in a case where the strip comprises the multilayer elastic strip. It is preferable to spiral a strip in the direction by which the strip is loosened as the drive shaft rotates in a case where the strip comprises the monolayer elastic strip. FIG. 4 shows a monolayer coil and a clockwise rotation of the drive shaft. The elastic member 19 extends to be inserted into a coil-like elastic member 41, which is connected at a free end of the outer sheath, by about 0.5 to 20 mm long.

Material to form the coil-like elastic members 19 and 41 is similar to that mentioned above.

Signal lines 7a and 7b are connected with electrodes on each surface of the oscillator 3, respectively. The signal cables may be combined into a coaxial line as well as a stranded line in FIG. 4.

The outer sheath 2 of the catheter 30 comprises a handle side (a shaft body) 15 and a tip side (a tip portion) 12. An outer surface of a tip portion of the handle side 15 is treated to taper its thickness towards the tip. An inner surface of a proximal portion of the tip side 12 is treated to taper its thickness towards the proximal end. The tip portion of the main body 15 thus configured is inserted into a proximal end of the tip portion 12 and secured to each other to form a connecting portion. The connecting portion thus formed has an almost even outer diameter therethrough. The connecting portion thus formed realizes a relatively long connecting portion, high strength in the connecting portion. And, furthermore, the connecting portion has no point in which a mechanical property varies radically, that is the mechanical property varies gradually through the connecting portion. The outer sheath 2 is thereby improved through the connecting portion in bending, flexibility and so on.

The resin cover 17 is disposed at the tip of the ultrasonic imaging catheter 30 to cover a difference in level between the tip portion 12 of the sheath and a portion of the elastic member 41 projected from the tip portion 12. A free end of the resin cover 17 is formed conical as well as that of the free end of the elastic member 41. The resin cover 17 assists the free end of the elastic member in keeping its shape. The resin cove 17 is made of flexible synthetic resin such as silicone rubber, polyurethane, olefin system elastomer, polyamide elastomer.

Figure 6:
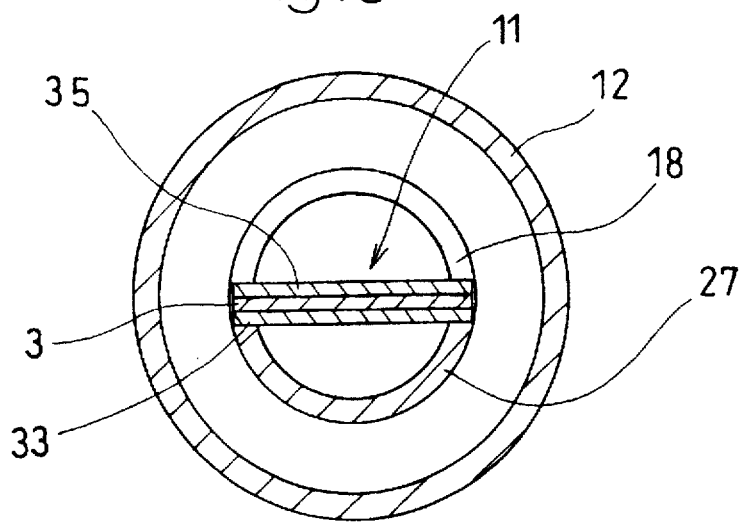
FIG. 6 is a sectional view along an 6—6 line in FIG. 4.

As shown in FIGS. 5 and 6, the housing 27 of pipe-shaped configuration has a fixing portion 18 of the transducer 11 that is formed by cutting the pipe-like member in an axial direction around the center by a predetermined length and IN a radial direction by almost a half of a circle of the pipe-like member. The transducer 11 is set into the fixing portion 18 as directing an acoustic alignment layer 35 to an open side of the fixing portion and a back layer 33 to a bottom side of the fixing portion. The transducer 11 is secured to the housing 27 with an adhesive.

Figure 7:
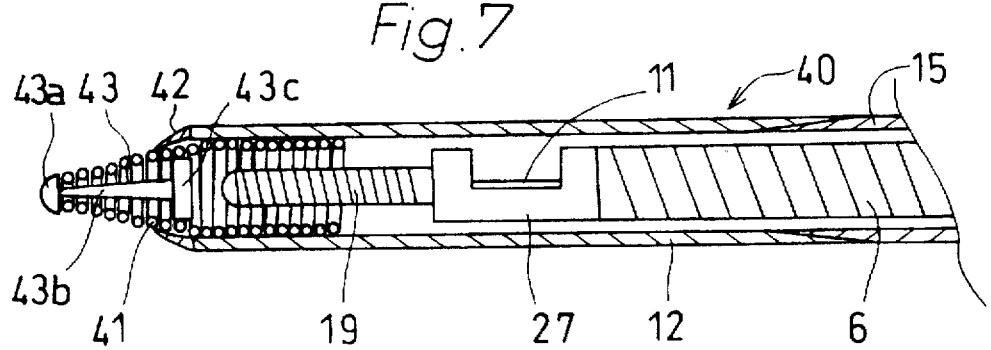
FIG. 7 is a sectional view of an ultrasonic imaging catheter of another embodiment of the present invention.

Next, explanation for an ultrasonic imaging catheter 40 of another embodiment shown in FIG. 7 will be made.

In the ultrasonic imaging catheter 40 of the embodiment, a coil-like elastic member 19 is connected to a free end of a housing 27. The member 19 is made of metal such as stainless steel (SUS304, SUS316, etc.), Ni—Ti system alloy. A coil-like member 41 having a X-ray contrast is attached inside of a tip portion 12 of an outer sheath by an adhesive 42. A free end of the elastic member 19 is so formed that it is positioned within the coil-like member 41. A free end of the coil-like member 41 tapers in diameter towards the tip of the catheter. A supporting member 43 is disposed in the free end of the coil-like member 41. The supporting member comprises a wire portion or at least a plate portion. It is preferable to form the supporting member 43 with metal such as stainless steel (SUS304, SUS316, etc.), Ni—Ti system alloy. The supporting member 43 improves the mechanical strength or flexibility of the coil-like member 41. The supporting member 43 comprises a hemisphere-like tip portion 43a, a connecting portion 43b extending in a rear direction from the hemisphere-like tip portion 43 with an increasing diameter, and a disk portion 43c formed at the rear end of the connecting portion 43b. A circumferential surface of the disk portion 43c is engaged with an inner surface of the coil-like member 41. A tip of the coil-like member 41 is in contact with a rear surface of the hemisphere-like tip portion 43a.

Figure 8:
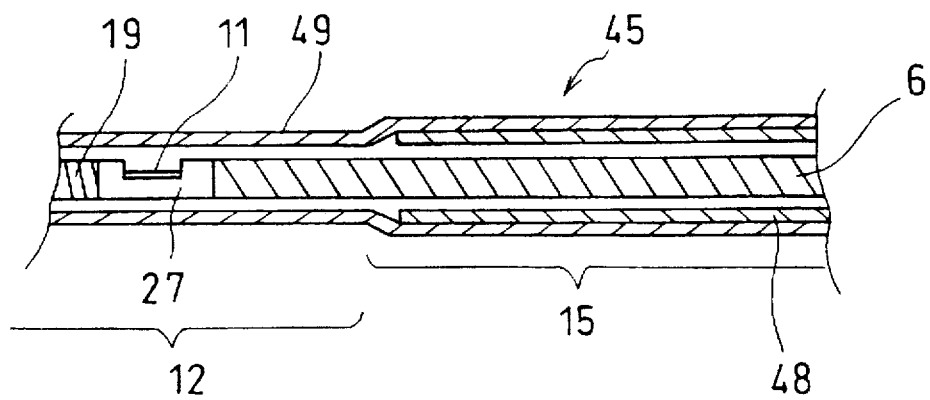
FIG. 8 is a partially sectional view of an outer sheath used for the ultrasonic imaging catheter of the present invention.

The configuration of the outer sheath is not limited to the above mentioned and a configuration of the catheter 45 shown in FIG. 8 is also available. FIG. 8 is a sectional view showing a part of modified outer sheath used for the ultrasonic imaging catheter 45 of the present invention. In the outer sheath, a handle side (a main body) 15 comprises two layers of an inner layer 48 and an outer layer 49. A tip side 12 including an ultrasonic wave transmitting-receiving unit is formed with only the outer layer 49. The inner layer 48 of the handle side (the main body) 15 is formed with metallic tube of stainless steel (SUS304, SUS316, etc.), super elastic metallic tube of Ni—Ti system alloy or tube configured by spiraling stainless steel (SUS304, SUS316, etc.) strip in a coil manner or in a blade manner. The outer layer 49 is formed with resin such as polyolefin system resin, fluoride system resin or polymer. The outer layer 49 is formed as follows. That is, inserting an inner tube into a heat shrinkable tube as the outer layer and heating them to shrink the outer heat shrinkable tube to coat the inner tube. Inserting an inner tube into a resin tube, which is swelled by a solvent, as the outer layer and drying the solvent to shrink the outer resin tube to coat the inner tube. Dipping the inner tube with resin to be the outer layer to coat the inner tube. Extruding melted resin to be the outer layer on an outer surface of the inner tube to coat the inner tube.

Explanation of an ultrasonic imaging catheter 50 of another embodiment of he present invention will be made by referring to FIGS. 9, 10, 11 and 12. The basic configuration of the ultrasonic imaging catheter 50 is identical with the ultrasonic imaging catheter 1 shown in FIGS. 1 and 2. A handle portion (a connector) of the ultrasonic imaging catheter 50 is, in particular, identical with that shown in FIG. 2.

The ultrasonic imaging catheter 50 of this invention comprises an outer sheath 2 to be inserted into a body cavity, a drive shaft 6 inserted into the outer sheath 2, a housing 27 secured at a tip of the drive shaft 6, a handle portion (a connector) 20 of a handle side connected with a proximal end of the outer sheath 2.

Figure 9:
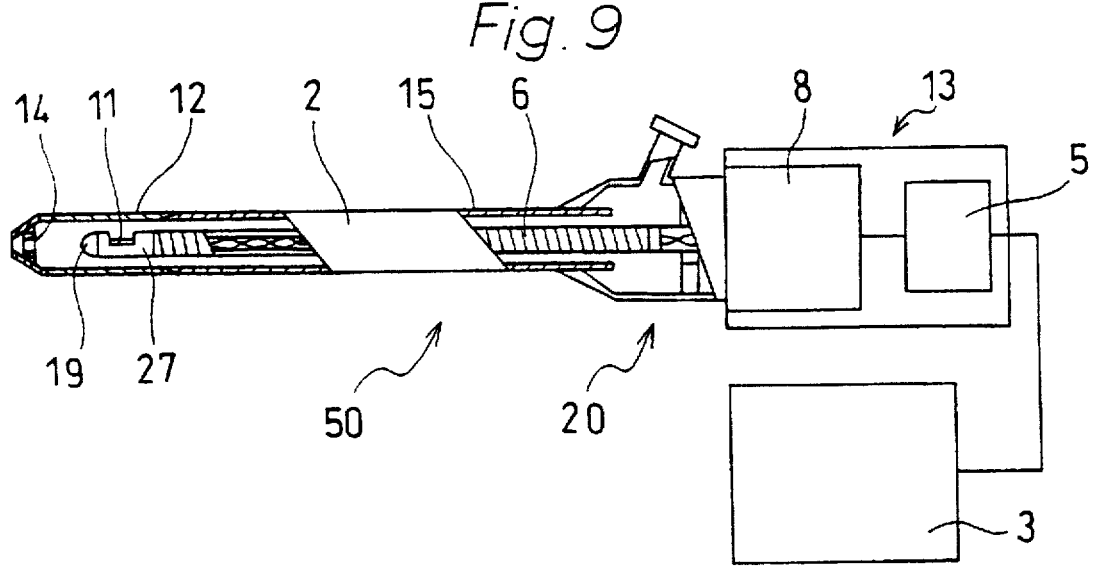
FIG. 9 is a partially sectional view of an ultrasonic imaging catheter of another embodiment of the present invention attached to an outer unit.

FIG. 9 shows an ultrasonic imaging catheter system configured by attaching the ultrasonic imaging catheter 50 to an outer unit 13.

A housing 27 is disposed in a tip side of the outer sheath 2 of the catheter and a transducer 11 having a function as an ultrasonic wave oscillator for transmitting and receiving an ultrasonic wave is disposed in the housing 27. The housing 27 is made tom a hollow pipe of a cylindrical shape. A part of the pipe is cut to be a gutter-like portion 18 and in which the transducer 11 is secured. The housing 27 is connected at a free end of the coil-like drive shaft 6. A metallic piece 14 giving a good X-ray contrast is located at the tip portion of the outer sheath.

The drive shaft 6 is formed with two layers of plates spiraled twice and the plates are made of stainless steel (SUS304, SUS316, etc.) or the like. The drive shaft preferably has breaking strength of 0.4 kgf or more. The drive shaft 6 may be formed with a wire or a plate, which is made of metal or resin, spiraled once or multiply in a coil manner or in a blade manner. The drive shaft may be formed by winding a signal cable mentioned below around the wire having the breaking strength of 0.4 kgf for more.

The signal cable 7 formed by stranding two leads is disposed in the drive shaft 6. An end of the signal cable 7 positioned at the tip of the catheter is connected with an oscillator formed in the transducer 11. Another end of the signal cable 7 positioned at the proximal end (at the handle side) of the catheter is connected with terminals 21 and 22 on the handle portion 20. In more detail, as shown in FIG. 2, the terminals 22 and 23 are provided to the tubular member formed of a insulating material is inserted and fixed into a rear end of the drive shaft 6. A proximal end of the lead 7a is connected with the terminal 22. A proximal end of the other lead 7b is connected with the terminal 21.

The handle portion (the connector) 20 has, as shown in FIG. 2, a projection 25 to be engaged with an arresting member 13a of the outer unit 13. The projection 25 and the arresting member 13a are connected in a detachable manner.

The motor 16 as an outer driving source has a rotor (a rotating plate) 16a. A first cylindrical terminal 24 is secured at the center of the rotating plate 16a and a second cylindrical terminal 23 is secured on the rotating plate 16a around the first cylindrical terminal 24 without any contact therebetween. The cylindrical terminals 23 and 24 rotate together with the rotating plate.

A rotational slip terminal member 26 that comprises a slip ring or the like connected with the transmitting-receiving circuit 5 is disposed inside the outer unit 13. The terminal member 26 has a first terminal 26a and a second terminal 26b. The first terminal 26a is in contact with the second cylindrical terminal 23 on the rotational plate. The second terminal 26b is in contact with the first cylindrical terminal 24 on the rotational plate. The contacts between the respective terminals are kept while the rotational plate rotates.

The tubular member 22 secured to the drive shaft 6 is engaged with an opening of the first cylindrical terminal 24 on the rotational plate. The proximal portion (terminal 21) of the tubular member is allowed to enter the second terminal 23 on the rotational plate and the proximal portion is engaged with a circular rib formed near the free end of an opening of the cylindrical terminal 23. The drive shaft 6, thereby, is connected with the rotational plate of the motor 16 in a detachable manner. Rotational force of the motor is hence transmitted to the drive shaft through the rotational plate and two cylindrical terminals 23 and 24.

The outer unit 13 comprises a transmitting-receiving circuit 5 and a driving source 8 including a motor 16. The outer unit 13 is electrically connected with a console 3 having a signal processing circuit and an image displaying system.

The transducer 11 mentioned above is available.

Figure 10:
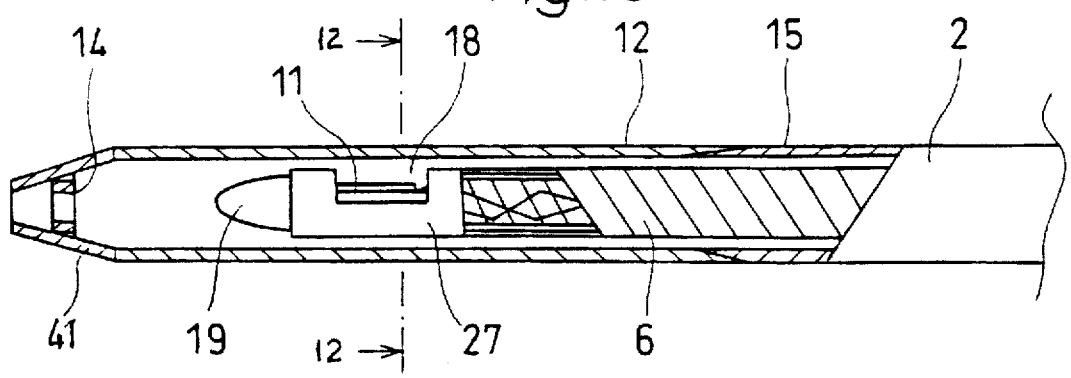
FIG. 10 is an enlarged and sectional view of a tip portion of the ultrasonic imaging catheter shown in FIG. 9.
Figure 11:
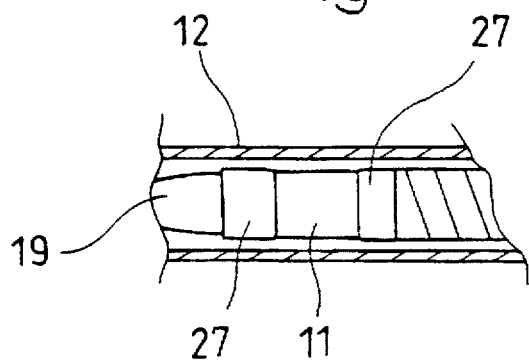
FIG. 11 is a plane view showing a transducer of the ultrasonic imaging catheter shown in FIG. 10 and vicinities of the transducer.
Figure 12:
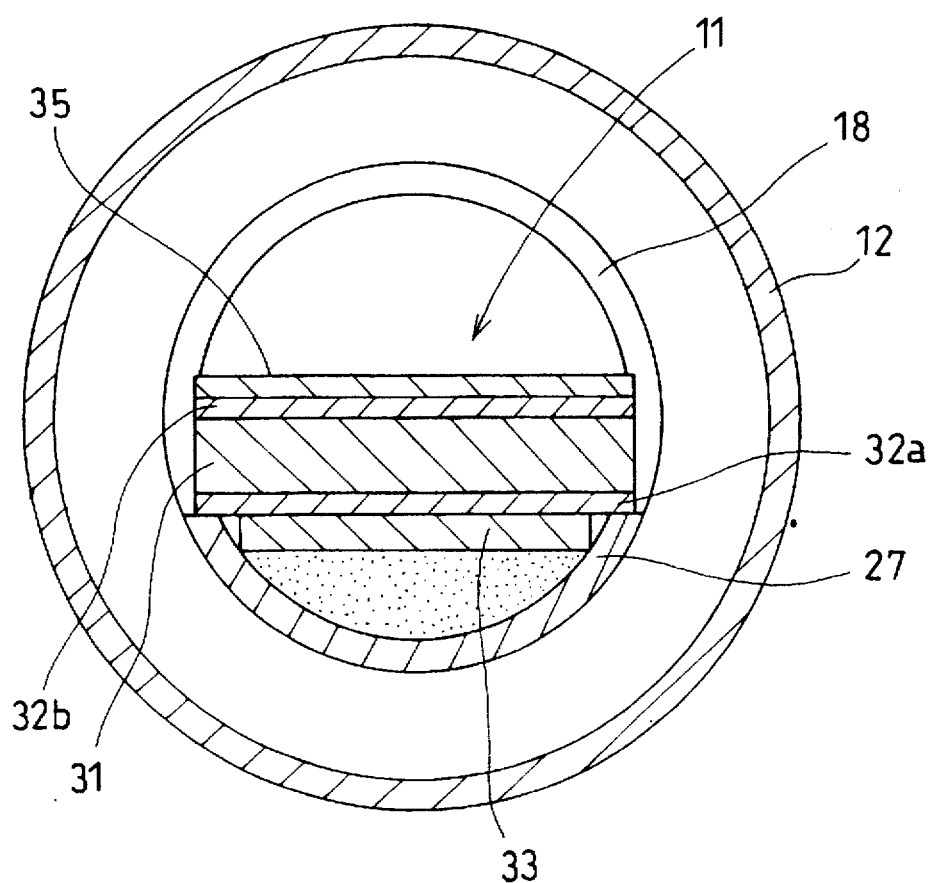
FIG. 12 is an enlarged and sectional view taken along a line 12—12 in FIG. 10.

As shown in FIGS. 10, 11 and 12, the housing 27 secured to the drive shaft 6 is pipe-shaped and has a diameter approximately equal to that of the drive shaft 6. A portion of the housing is cut as a gutter shape to form a fixing portion 18 of the transducer 11. That is, the cylindrical housing 27 has a cut portion for receiving the ultrasonic wave oscillator at a center in the axial direction. The oscillator (the transducer 11) is housed in the cut portion as contacting to the housing 27. The cut portion is an opening formed on a side surface of the housing 27 by cutting a central portion of the cylinder by a predetermined length in an axial direction and about a half of a circle in the radial direction.

The housing is made of insulating material. The insulating material is ceramics such as alumina and zirconia in preferable. Fabrication of the housing 27 with the ceramics is carried out as follows. At first, a raw material that has been made sufficiently small (minute) to extrusion molding to form a pipe-like work, followed by heating and sintering the work to form a ceramic pipe. The ceramic pipe is cut in the radial direction and in the axial direction by utilizing an abrasive and treating machine such as a dicing saw or a wire saw to form a gutter-like portion (the cut portion) for securing the transducer 11 therein. The transducer 11 is secured to the gutter-like portion by epoxy system adhesive, ceramic system adhesive, cyanoacrylate system adhesive or the like. An electrode 32a of the transducer 11 fixed to housing 27 as show in FIG. 12 may make contact with housing 27.

The rod-like elastic member 19 is connected at the tip portion of the housing 27 by an adhesive agent. The elastic member 19 is made of elastic metal such as stainless steel (SUS304, SUS316, etc.), super elastic metal such as Ni—Ti system alloy and resin such as polyacetal. A tip member 41 of the catheter is so treated that it tapers in diameter towards the tip there of A ring-like member 14 is disposed inside of the tip member 41 and the member 14 is made of metal such as Pt, Ir, Au or the like or alloy thereof to give a X-ray contrast. The tip member 41 of the ultrasonic imaging catheter 50 has an opening at the free end thereof, but the member 41 may be formed without the opening. The tip member 41 may be formed as a different piece from the outer sheath 12. A coil-like elastic member having the contrast can be substituted for the ring-like member 14 to form a tip member.

The remainder configuration, e.g. the configuration of the outer sheath is identical to that of the ultrasonic imaging catheter 1 mentioned above. The structure shown in FIGS. 4, 5 and 6 or FIG. 7 is applicable to the ultrasonic imaging catheter 50 of the present invention. In the ultrasonic imaging catheter 50 of the present embodiment, the outer sheath thereof may be modified to the shape and configuration as shown in FIG. 8.

Explanation for an ultrasonic imaging catheter 100 of another embodiment of the present invention be made by referring to FIGS. 13, 14, 15, 16, 17 and 18.

Figure 13:
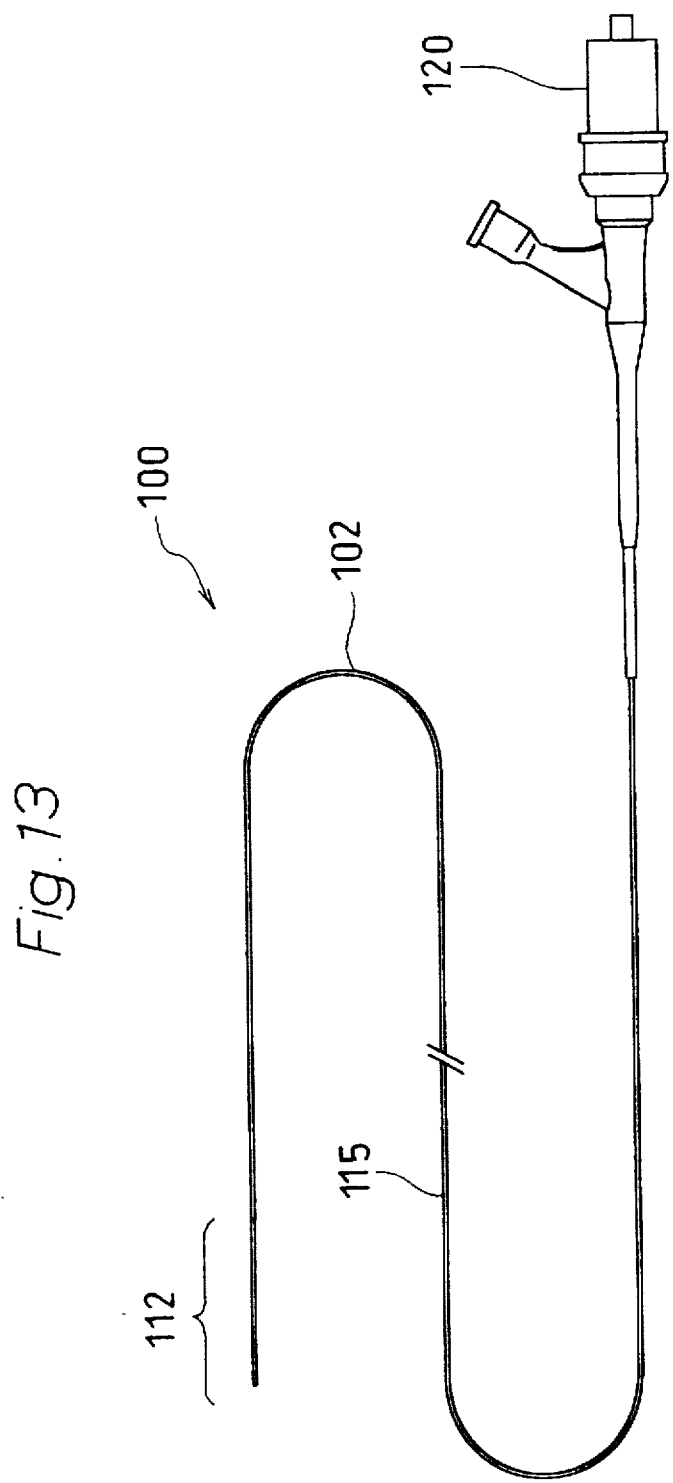
FIG. 13 is a perspective view of an ultrasonic imaging catheter of another embodiment of the present invention.

The ultrasonic imaging catheter 100 of the present embodiment comprises, as shown in FIGS. 13 and 15, an outer sheath assembly 102 to be inserted into the body cavity, a drive shaft assembly 106 inserted into the outer sheath assembly 102, and a connector 120 secured to a proximal end of the outer sheath assembly 102.

The outer sheath assembly 102 comprises a tip portion 112 and main body 115. The tip portion 112 of the outer sheath assembly 102 comprises a tip-center portion 112b having a coil-like elastic member 141, a tip end portion 112a and a tip base portion 112c (an ultrasonic wave transmitting and receiving portion) having no elastic member 141 in front of and in the rear of the center portion 112b. A transducer 11 is disposed inside of the tip base portion 112c.

A tip member 117 is connected at the tip of the outer sheath assembly 102. A through hole 117a provided at the tip member 117 communicates the outer space and the inner space of the outer sheath assembly 102. The tip member 117 shaped as a hemisphere on the tip side thereof is secured at the free end of the outer sheath assembly 102. A coil-like elastic member (a first elastic member) 141 is provided in the outer sheath assembly 102. The elastic member 141 extends a predetermined length towards the proximal end side from a position slightly shifted to the proximal end side from the free end of the outer sheath assembly 102. The coil-like elastic member 141 is fixed by being sandwiched between an outer layer 102a and an inner layer 102c forming the outer sheath assembly 102. The coil-like elastic member 141, therefore, is not exposed so that the catheter 100 is improved m movement in a guiding catheter. The result is that the top of a catheter is flexible, because the flexibility member 141 in the form of coil does not exist in top part. It decreases the possibility that an inner wall of a blood vessel receives damage by the top of a catheter, when the top of a catheter makes contact with the inner wall of a blood vessel by this.

Figure 19:
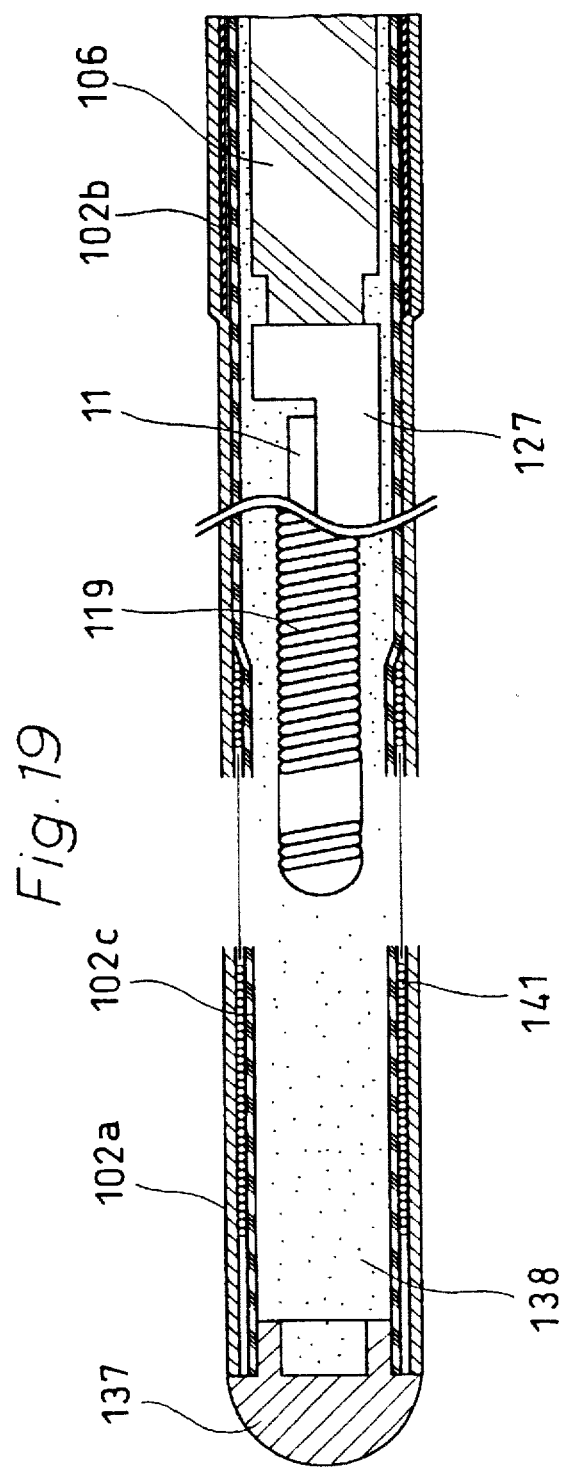
FIG. 19 is an enlarged and sectional view of the tip portion of the catheter of another embodiment of the present invention.
Figure 20:
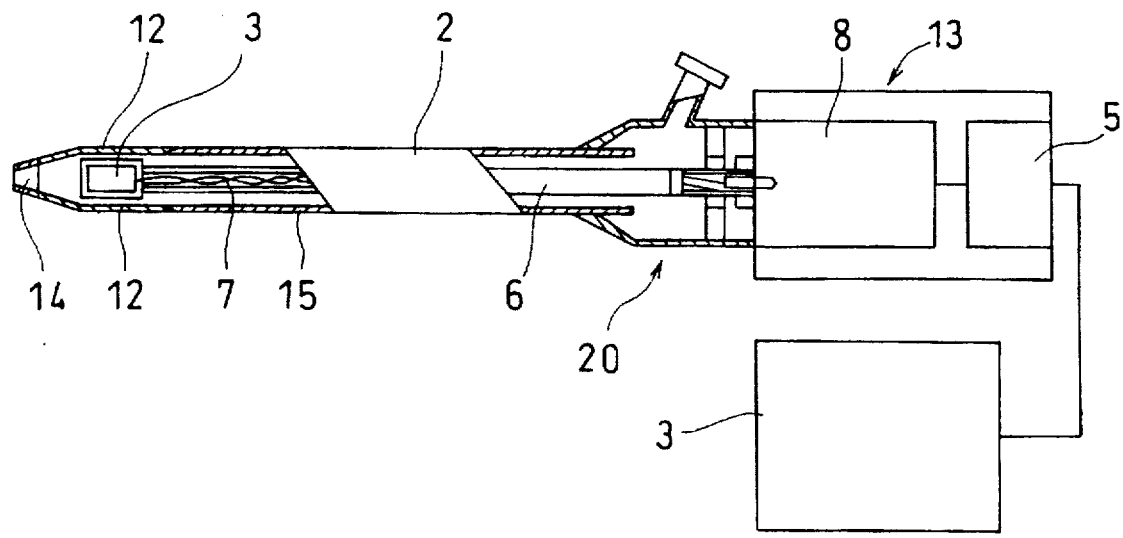
FIG. 20 is a partially sectional view of a conventional ultrasonic imaging catheter attached to an outer unit.
Figure 21:
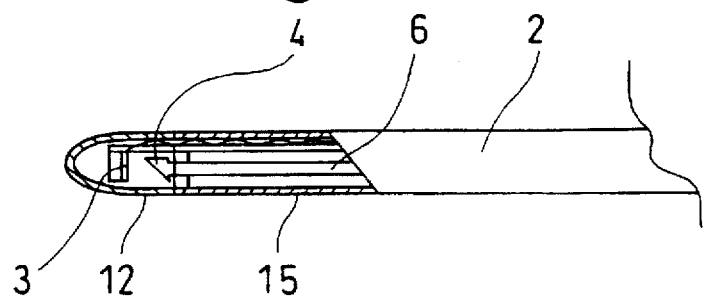
FIG. 21 is a sectional view of a tip portion of the conventional ultrasonic imaging catheter.

It is useful to also provide a tip member 137 that does not have the through hole like the catheter shown FIG. 19. In this case, a closed inner space of a catheter may fill up a harmless liquid 138 to such a living body as isotonic sodium chloride solution. The result of this is that priming work at the time of use of the catheter is useless.

The length of the coil-like elastic member 141 is preferably 5 to 50 mm, and 10 to 30 mm more preferably, but it depends on the length of the whole catheter. The length of a distal portion 112a without the elastic member 141 may be 1 to 10 mm, 1 to 5 mm preferably. The elastic member 141 can extend up to the free end of the outer sheath assembly 102. The coil-like elastic member 141 is preferably made of metal, in particular, material (metal) of producing a high contrast in an image formed with an X-ray such as metal of Pt, Ir, Au, etc., alloy thereof or the like.

The outer sheath assembly 102 is a tube-like member of multi layers as shown in FIG. 15. The assembly 102 has at least an outer layer 102a and an inner layer 102c that extend from the proximal end of the outer sheath assembly to the tip end thereof. The main body 115 of the outer sheath assembly 102 includes the outer layer 102a, the inner layer 102c and an intermediate layer 102b between the outer layer 102a and the inner layer 102c. The tip base portion 112c and the tip end portion 112a comprise only the outer layer 102a and the inner layer 102c. The intermediate layer 102b is a reinforcement layer and made of stiff materials.

Resin being good in permeability of the ultrasonic wave is preferable for the material of the outer layer 102a and the inner layer 102c of the outer sheath assembly 102. That is, polyolefin system resin, polyurethane system resin, fluoride system resin or the like is available. Polyethylene, factually low density polyethylene for the outer layer and high density polyethylene for the inner layer, is more preferable. Thickness of the portion 112c for the ultrasonic wave transmitting and receiving in the outer sheath assembly is about 10 to 100 μm in preferable. A tube made of rigid resin, elastic metal, super elastic metal or the like is available for the reinforcement layer 102b.

The following material is available for the elastic metal That is substantial metal such as steel, tungsten, copper, etc., or alloy thereof (such as austenitic system stainless steel, for example, SUS304, SUS316and SUS321, maraging stainless steel Cu—Zn alloy and Cu—Sn alloy). The austenitic system stainless steel is more preferable.

Super elastic metal means alloy generally called a shape-memory alloy which shows a superelasticity at the body temperature (around 37° C.). Super elasticity here means the capability of super elastic metal to recover almost its former shape at the temperature at which it is used after it is deformed (bent, elongated or compressed) to such a degree that ordinary metal undergoes permanent deformation. Preferable superelastic alloys include Ti—Ni binary alloy consisting essentially of 49 to 58 atom percents of Ni (the balance of Ti), Cu—Zn binary alloy consisting essentially of 38.5 to 41.5 wt. of Zn (the balance of Cu), Cu—Zn-X ternary alloy obtained by replacing part of Cu—Zn alloy with 1 to 10 wt % of X (X=Be, Si, Sn, Al or Ga), and Ni—Al binary alloy consisting essentially of 36 to 38 atom percents of Al (the balance of Ni). Of these alloys, Ti—Ni binary alloy is especially preferable. The mechanical property of Ti—Ni alloy can be changed as desired by replacing part of Ti—Ni alloy with 0.01 to 2.0 atom percents of X (X=Co, Fe, Mn, Cr, V, A, Nb, Pd B, etc.).

The intermediate layer 102b includes a spiral slit extending from a tip end toward the other end, A tip portion of the intermediate layer has the slit and the remainder portion of the intermediate layer has no slits. The tip portion of the intermediate layer is a deformable portion which is more flexible than the remainder. The tip portion of the elastic metal tube is flexible in that its side wall is deformable radially inward. The spiral slit is preferably formed such that each width of the slit tapers or decreases gradually from the tip end toward the other end, that is the width widens or increases gradually toward the tip side. Each of the slits has the maximum width at the tip end of the elastic metal tube. The deformability of the elastic metal tube, therefore, increases toward the tip thereof. Preferably one to three slits are formed with approximately even pitch. Also preferably, the slit has a maximum width of about 0.05 to 0.5 mm at the tip end (as measured m a circumferential direction). The width of the slit is preferably about ⅙ to ⅓, more preferably about ⅕ to ¼ of the outer diameter of the elastic metal tube.

The pitch between the spiral slit may be varied such that the pitch is shorter at the tip end and is longer at the proximal end. Where the pitch of the slit varies, the pitch is preferably about 0.3 to 3.0 mm at the tip end and about 5 to 10 mm at the proximal end. In an intermediate region of the elastic metal tube between the tip end and the other end, the pitch of the slit is an intermediate value of the both ends or changes gradually in preferable. Preferably the slit has the varying pitch and the varying width as described above.

The slit is formed in the metal tube by any of conventional techniques including laser machining (e.g., YAG laser), electric discharge machining, chemical etching, machining, and combinations thereof.

It is possible to coat an outer surface and an inner surface of the outer sheath assembly with hydrophile resin, fluoride resin or silicone resin or the like in 1 to several tens μm thickness. The sliding resistance of the outer and inner surfaces of the outer sheath assembly decreases by the treatment mentioned above. In addition, it is possible to coat or fix the outer surface of the outer sheath assembly with antithrombus material. Coating with the antithrombus material is realized by coating the outer surface of the assembly with a resin including the antithrombus such as heparin. It is preferable that the outer surface of the outer sheath assembly 102 has high lubricity or wettability, which reduces the sliding friction and makes easier the insertion into a hollow organ or the body cavity of the living body. The high lubricity or wettability is realized by introducing an appropriate kind of functional group into a resin coat of the outer layer 102a. Thereafter, coating or fixing the resin coat with polymer having the high lubricity or wettability. Hydrophile polymer such as Poly(2hydroxyethyl metacrylate), polyhydxoxyethylacrylate, hydroxypropyl cellulose, methyl vinyl ether-maleic anhydride copolymer, polyethyleneglycol, polyacrylamide and polyvinylpyrrolidone or the like is available as the polymer having the high lubricity or wettability.

Figure 16:
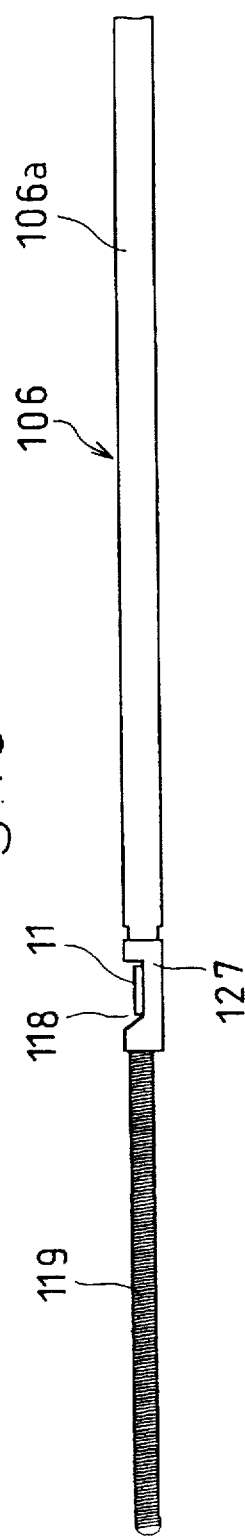
FIG. 16 is an enlarged view showing an end portion of an assembly of drive shaft for the catheter shown in FIG. 13 and vicinities of the end portion.

The drive shaft assembly 106 comprises, as shown in FIG. 16, a shaft body 106a, a housing 127 for a transducer secured to a tip end of the shaft body 106a, and a rod-like elastic member 119 secured to a free end of the housing 127.

The elastic member 119 is a rod-like member made of elastic metal such as stainless steel, super elastic metal, resin such as polyacetal or the like. The super elastic metal or the elastic metal is, in particular, preferable. The mentioned above is available for the superelasic metal. The rod-like member of the present embodiment is shaped like a coil due to its high flexibility.

The second elastic member 119 of the drive shaft assembly 106 is approximately 2 to 30 mm long preferably. It is more preferably 3 to 20 mm long. A free end of the second elastic member 119 is, as shown in FIG. 15, inserted into a proximal end portion of the first elastic member 141. That is, the fee end of the second elastic member 119 is located inside of the first elastic member 141. The elastic member 141 and the elastic member 119 reinforce with each other. Therefore, a change in physical property around the proximal end portion of the coil-like elastic member 141 is smoothed. It is thereby prevented that the catheter kinks around the proximal end portion of the coil-like elastic member 141. In a similar manner, a change of physical property of the catheter around the free end of the elastic member 119 is smoothed by the coil-like elastic member 141. It is thereby prevented that the catheter kinks around the free end of the elastic member 119. The elastic member is preferably inserted into the portion in which the coil-like elastic member 141 is formed by approximately 0.5 to 20 mm long. The elastic member 119 is connected with the free end of the housing 127 by adhering, brazing, welding or the like.

The drive shaft body 106a is formed with two layers of plates spiraled twice and the plates are made of stainless steel (SUS304, SUS316, etc.) or the like. The drive shaft body preferably has breaking strength of 0.4 kgf or more. The drive shaft body 106a may be formed with a wire or plate, which is made of metal or resin, spiraled once or multiply in a cot manner or in a blade manner. The drive shaft body may be formed by winding a signal cable mentioned below around the wire having the breaking strength of 0.4 kgf or more.

Factually, the drive shaft body 106a comprises a coil. For the material of the drive shaft body, the aforementioned superelastic alloy and stainless steel such as precipitation hardening (PH stainless steel, especially semiaustenitic) stainless steel and maraging stainless steel are preferable. The number of layers of winding of the coil is not limited to one. A multi-layer structure consisting of two or more layers is preferable in order to increase torque transmissibility. In such a multilayer structure, it is preferable to reverse the direction of winding alternately layer by layer. By this structure, the drive shaft body is improved in transmissibility of pressure given on the proximal end of the catheter and is also improved in torque transmissibility.

Figure 17:
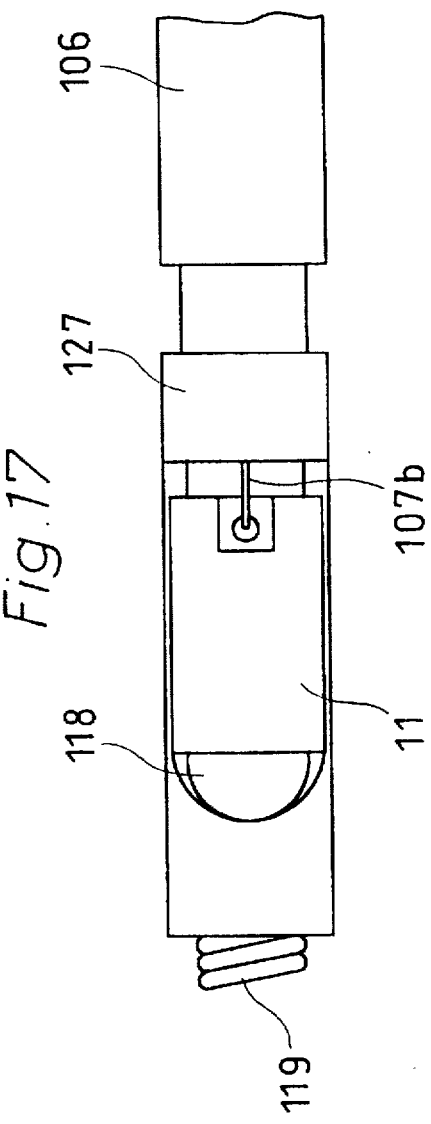
FIG. 17 is a plane view showing a transducer of the assembly of the drive shaft shown in FIG. 16 and vicinities of the transducer.
Figure 18:
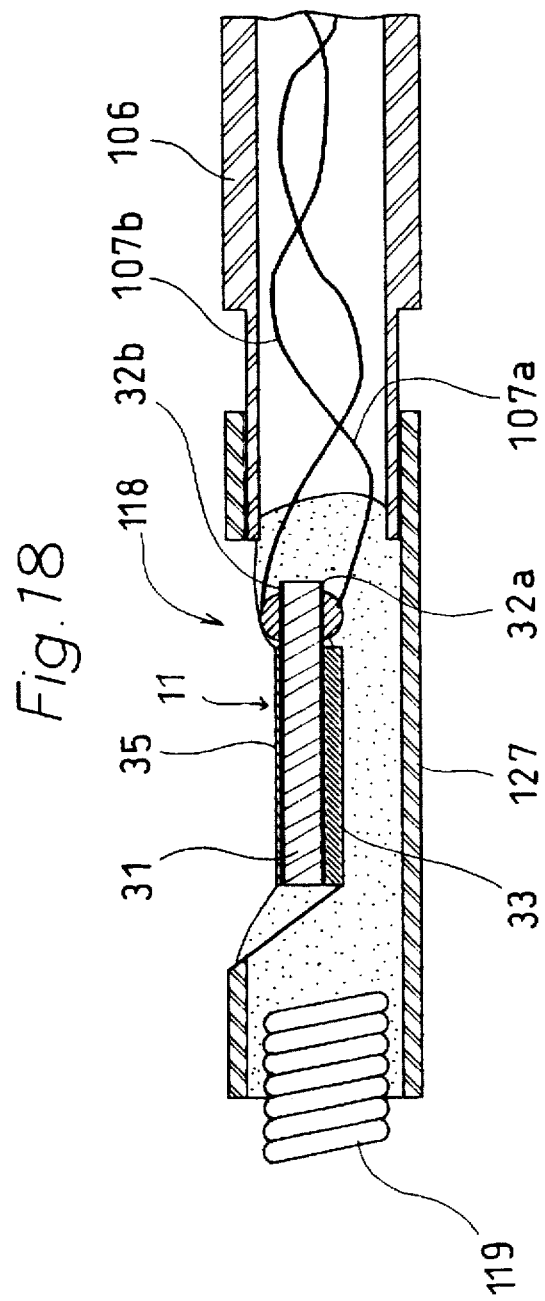
FIG. 18 is a sectional view of the assembly of the drive shaft shown in FIG. 17.

As shown in FIGS. 17 and 18, the housing 127 for receiving the transducer 11 is a cylindrical member having a diameter approximately equal to that of the drive shaft body 106a. The housing 127 has a fixing portion 118 for the transducer 11 and the fixing portion 118 is formed by cutting a side surface of the cylindrical member in an axial direction around the center by a predetermined length and in a radial direction by almost half of a circle of the cylindrical member. A tip-side wall of the fixing portion of the present embodiment inclines. For the material of the housing 127, metal, resin, ceramics or the like is available. A tip end portion of the drive shaft body 106a is formed smaller in diameter than the remainder. The tip end portion is inserted into a proximal end of the housing 127. It is preferable to interpose insulating material between the tip end portion of the drive shaft body and the housing 127 in a case where the housing 127 is made of conducting material.

The transducer 11 is so housed in the fixing portion that an outer surface of an ultrasonic wave transmitting-receiving surface as exposed. For the transducer 11, the one shown in FIG. 3B is available. The transducer 11 is housed in the housing 127 and fixed thereto with adhesive as being its acoustic alignment layer 35 outside and its back layer 33 inside of the housing 127 as shown in FIG. 18. Stranded signal cables 107a and 107b, which are connected with the electrodes 32a and 32b of the transducer 11 respectively; are threaded into the drive shaft body 106a. Each of the signal cables are connected with terminals (not shown) of a connector 120 at their proximal end (handle side). The handle portion (the connector) 120 is configured similar to that shown in FIG. 2.

An explanation of ultrasonic wave scanning by the ultrasonic imaging catheter of the present invention will be made hereinbelow. The explanation to the ultrasonic wave scanning will be made by referring to FIG. 1, but it covers all of the embodiments mentioned above.

The motor 16 inside of the outer unit 13 rotates to make a rotational movement and the rotational movement is transferred to the drive shaft 6 through the terminals 21 ad 22 in the connector 20 of the catheter. The housing 27 secured to the tip end of the drive shaft 6 is thus rotated as performing transmitting and receiving of the ultrasonic wave by the transducer. The ultrasonic wave transmitted and received by the transducer 11 is scanned in a radial direction of the catheter 2 to reconstruct an ultrasonic wave image. The ultrasonic wave image thus obtained is a sectional image or a tomogram in the radial direction of the vessel and the vas. A tomogram in an axial direction of the vessel and vas may be reconstructed by moving the ultrasonic imaging catheter in the axial direction thereof. The tomogram in the axial direction is also obtained by constructing the catheter and the outer unit to move the drive shaft 6 in the axial direction of the catheter.

An explanation of a method of handling the ultrasonic imaging catheter of the present invention in the blood vessel will be made hereinbelow.

The handling of the ultrasonic imaging catheter is similar to that of a conventional blood catheter. That is, inserting an introducer or the like into a blood vessel form outside of a living body. A guiding catheter, through which a guide wire is threaded, is inserted into the introducer. The ultrasonic imaging catheter of the present invention is inserted into the guiding catheter after the tip of the guide wire arrives at an object portion to be diagnosed or treated. Thereafter, the tomogram of the vessel is reconstructed according to the ultrasonic wave handling method mentioned above. The guide wire may be remained inside the guiding catheter or pulled out from the guiding catheter as reconstructing the tomogram. The handling of the ultrasonic imaging catheter of the present invention is not limited to the case where the guiding catheter is used. The ultrasonic imaging catheter of the present invention may be inserted into a guide wire rumeen of a treating catheter such as a balloon catheter. In such a case, an outer diameter of the ultrasonic imaging catheter is 0.25 to 0.97 mm in preferable and 0.35 to 0.46 is more in preferable.

In the ultrasonic imaging catheter of the present invention, the free end of the second elastic member is inserted into the coil-like first elastic member. The portion between the housing and the coil at the tip portion of the catheter is reinforced to improve flexibility and kinking. Therefore, the catheter is improved in movement in the vessel or the vas of the body cavity and handling of the ultrasonic imaging catheter becomes preferable.

In the ultrasonic imaging catheter of the present invention, the housing for housing the ultrasonic wave oscillator is made of insulating ceramic material The insulation resistance of the housing is thus made high so that a short between the electrodes of the oscillator does not occur even when the oscillator is in directly contact with the housing. An oscillator largest in size but it is allowed to be set in the housing is available. Therefore, in a case where the present invention is applied to a thin ultrasonic imaging catheter of 1 mm or less in diameter, an ultrasonic wave oscillator of large enough for such a size of the catheter is available. It is thereby realized to be deeper in depth of transparency of the ultrasonic wave in the object and smaller in divergence of the azimuth direction.

Although the invent/on has been disclosed in the context of certain preferred embodiments, it will be understood that the present invention extends beyond the specifically disclosed embodiments to other alternative embodiments of the invention. Thus it is intended that the scope of the invention should not be limited by the disclosed embodiments, but should be determined by reference to the claims that follow.

We claim:

1. An ultrasonic imaging catheter comprising:
   an outer sheath insertable into a body cavity, said outer sheath having a tip side and a tip portion;
   a drive shaft positioned in the outer sheath for transmitting mechanical driving force from a proximal side to a tip side of the drive shaft, the drive shaft being rotatable by an outer driving source;
   a housing secured to the drive shaft in which an ultrasonic wave oscillator or both the ultrasonic wave oscillator and an ultrasonic wave reflector are disposed, the housing having a tip portion and the housing being located inside the outer sheath at the tip side of the outer sheath;
   a first elastic member disposed at the tip portion of the outer sheath; and
   a second elastic member disposed at the tip portion of the housing, the second elastic member extending toward a tip side of the catheter and up to a position inside the first elastic member so that a tip portion of the second elastic member is located inside of the first elastic member to reinforce the first elastic member.

2. An ultrasonic imaging catheter according to claim 1, wherein the length of the tip portion of the second elastic member that is located inside the first elastic member is 0.5 to 20 mm.

3. An ultrasonic imaging catheter according to claim 1, wherein the second elastic member is a coil-like elastic member.

4. An ultrasonic imaging catheter according to claim 1, wherein the outer sheath has a reinforcement layer having a spiral slit provided at a tip portion of the reinforcement layer.

5. An ultrasonic imaging catheter according to claim 1, wherein at least a part of the second elastic member is made of superelastic metal.

6. An ultrasonic imaging catheter according to claim 1, wherein the first elastic member comprises a through hole communicating an inner space and an outer space of the catheter.

7. An ultrasonic imaging catheter according to claim 1, wherein the first elastic member is made of material having a high X-ray contrast and the second elastic member is made of metal having an elastic property.

8. An ultrasonic imaging catheter according to claim 1, wherein a diameter of the second elastic member tapers toward the tip portion.

9. An ultrasonic imaging catheter according to claim 1, wherein the diameter of the first elastic member tapers toward the tip portion.

10. An ultrasonic imaging catheter according to claim 1, wherein the first elastic member has a supporting member inserted in a tip portion of the first elastic member.

11. An ultrasonic imaging catheter according to claim 1, wherein the ultrasonic wave oscillator comprises an ultrasonic wave oscillating section included in an ultrasonic wave transducer.

12. An ultrasonic imaging catheter comprising:
   an outer sheath assembly having a tip side and a tip portion, the outer sheath assembly including an outer layer and an inner layer;
   a drive shaft located in the outer sheath assembly;
   a housing secured to the drive shaft and in which an ultrasonic wave oscillator is disposed, the housing being located inside the outer sheath assembly at the tip side of the outer sheath assembly, the housing having a tip portion;
   a first elastic member located at the tip portion of the outer sheath assembly and located between the outer layer and the inner layer, the first elastic member having a proximal end portion; and
   a second elastic member disposed at the tip portion of the housing, the second elastic member extending toward a tip side of the catheter, the second elastic member having a free end positioned in the proximal end portion of the first elastic member.

13. An ultrasonic imaging catheter according to claim 12, wherein the outer sheath assembly has a hemispherically shaped tip member connected to a tip of the outer sheath assembly said tip member having an opening.

14. An ultrasonic imaging catheter according to claim 12, wherein the outer sheath assembly has a closed tip member connected to a tip of the outer sheath assembly to define a closed inner space within the outer sheath assembly that is filled with a liquid.

15. An ultrasonic imaging catheter according to claim 12, wherein the outer sheath assembly includes a body portion extending from the tip portion, the body portion of the outer sheath assembly having a reinforcement layer between the outer layer and the inner layer.

16. An ultrasonic imaging catheter according to claim 15, wherein a portion of the outer sheath assembly located axially on one side of the housing is devoid of the first elastic member and a portion of the outer sheath assembly located on an opposite side of the housing is devoid of the reinforcement layer.

17. An ultrasonic imaging catheter according to claim 15, wherein the reinforcement layer has a tip portion provided with a spiral slit.

18. An ultrasonic imaging catheter according to claim 12, wherein the ultrasonic wave oscillator comprises an ultrasonic wave oscillating section included in an ultrasonic wave transducer.

19. An ultrasonic imaging catheter according to claim 12, wherein the first elastic member is made of a material having a high X-ray contrast and the second elastic member is made of an elastic metal or a super elastic metal.

20. An ultrasonic imaging catheter according to claim 12, wherein the outer sheath assembly has a tip end portion that is devoid of the first elastic member.

21. An ultrasonic imaging catheter according to claim 12, wherein the outer sheath assembly comprises a main body, the tip portion of the outer sheath assembly comprising a tip-center portion positioned between a tip end portion and a tip base portion, the first elastic member being located in the tip-center portion while the tip end portion and the tip base portion are devoid of the first elastic member, the ultrasonic wave oscillator being disposed inside the tip base portion.

22. An ultrasonic imaging catheter according to claim 1, wherein the housing is formed of an insulating material.

23. An ultrasonic imaging catheter according to claim 22, wherein the housing is formed of ceramics.

24. An ultrasonic imaging catheter according to claim 23, wherein the ceramics is alumina or zirconia.

25. An ultrasonic imaging catheter according to claim 22, wherein the housing is cylindrical and has a cut portion for receiving the ultrasonic wave oscillator at the center in an axial direction of the cylindrical housing, and the oscillator being so received in the cut portion to contact the housing.

26. An ultrasonic imaging catheter according to claim 22, wherein the ultrasonic wave oscillator comprises an ultrasonic wave oscillating section included in an ultrasonic wave transducer.

* * * * *

UNITED STATES PATENT AND TRADEMARK OFFICE
CERTIFICATE OF CORRECTION

PATENT NO. : 5,738,100

DATED : April 14, 1998

INVENTOR(S) : Hiroyuki YAGAMI et al

It is certified that error appears in the above-identified patent and that said Letters Patent is hereby corrected as shown below:

In Column 1, line 22, after "be" and before "found" insert -- easily --.
In Column 1, line 30, after "thereof" insert -- . --.
In Column 2, line 47, delete "tuner" and insert -- inner --.
In Column 2, line 63, after "thereof" insert -- , --.
In Column 5, line 67, after "19" insert -- is --.
In Column 6, line 16, delete "re" and insert -- are --.
In Column 8, line 1, delete "cove" and insert -- cover --.
In Column 8, line 4, delete "m" and insert -- in --.
In Column 8, line 8, delete "IN" and insert -- in --.
In Column 8, line 56, delete "polymer" and insert -- polyamide --.
In Column 8, line 67, delete "he" and insert -- the --.
In Column 9, line 20, delete "tom" and insert -- from --.
In Column 9, line 34, delete "for" and insert -- or --.
In Column 10, line 34, after "(minute)" insert -- is subjected --.
In Column 10, line 52, delete "there of" and insert -- thereof --.
In Column 11, line 36, delete "m" and insert -- in --.
In Column 12, line 40, delete "A" and insert -- Al --.
In Column 12, line 57, delete "m" and insert -- in --.
In Column 14, line 4, delete "cot" and insert -- coil --.
In Column 14, line 40, delete "as" and insert -- is --.
In Column 14, line 52, after "of" and before "ultrasonic" insert -- the --.
In Column 14, line 59, delete "ad" and insert -- and --.
In Column 15, line 27, delete "rumeen" and insert -- rumen --.

UNITED STATES PATENT AND TRADEMARK OFFICE
CERTIFICATE OF CORRECTION

PATENT NO. : 5,738,100
DATED : April 14, 1998
INVENTOR(S) : Hiroyuki Yagami, et. al.

It is certified that error appears in the above-indentified patent and that said Letters Patent is hereby corrected as shown below:

In Column 15, line 53, delete "invent/on" and insert --invention--.

Signed and Sealed this

Twenty-eighth Day of July, 1998

Attest:

BRUCE LEHMAN

Attesting Officer    Commissioner of Patents and Trademarks